United States Patent
Buisman et al.

(10) Patent No.: US 6,852,305 B2
(45) Date of Patent: Feb. 8, 2005

(54) PROCESS FOR THE PRODUCTION OF HYDROGEN SULPHIDE FROM ELEMENTAL SULPHUR AND USE THEREOF IN HEAVY METAL RECOVERY

(75) Inventors: Cees Jan Nico Buisman, Harich (NL); Henk Dijkman, Ijlst (NL)

(73) Assignee: Paques Bio Systems B.V., Balk (NL)

( * ) Notice: Subject to any disclaimer, the term of this patent is extended or adjusted under 35 U.S.C. 154(b) by 0 days.

(21) Appl. No.: 10/720,102

(22) Filed: Nov. 25, 2003

(65) Prior Publication Data

US 2004/0115120 A1 Jun. 17, 2004

Related U.S. Application Data

(63) Continuation of application No. 09/831,950, filed as application No. PCT/NL99/00705 on Nov. 16, 1999, now abandoned.

(30) Foreign Application Priority Data

Nov. 16, 1998 (EP) .............................. 98203853
Dec. 29, 1998 (EP) .............................. 98204462

(51) Int. Cl.[7] .............................. C12P 3/00; C01B 17/16
(52) U.S. Cl. .................... 423/564; 423/220; 423/437.1; 423/563; 423/DIG. 17
(58) Field of Search .................... 423/220, 563, 423/573.1, 561.1, 511, 564, 437.1, DIG. 17; 435/262

(56) References Cited

U.S. PATENT DOCUMENTS

| 737,579 | A | | 9/1903 | Burschell | |
|---|---|---|---|---|---|
| 4,354,937 | A | * | 10/1982 | Hallberg | 210/607 |
| 4,614,588 | A | * | 9/1986 | Li | 210/603 |
| 4,735,723 | A | * | 4/1988 | Mulder | 210/603 |
| 4,931,262 | A | | 6/1990 | Sonta et al. | |
| 5,298,163 | A | * | 3/1994 | Ehlinger | 210/603 |
| 5,366,633 | A | * | 11/1994 | Buisman | 210/614 |
| 5,474,682 | A | * | 12/1995 | Buisman | 210/610 |
| 5,518,619 | A | * | 5/1996 | Buisman | 210/611 |
| 5,587,079 | A | * | 12/1996 | Rowley et al. | 210/603 |
| 5,670,123 | A | | 9/1997 | Mileo et al. | |
| 5,922,204 | A | * | 7/1999 | Hunter et al. | 210/603 |
| 6,217,766 | B1 | * | 4/2001 | Stetter et al. | 210/605 |
| 6,228,263 | B1 | | 5/2001 | Rose et al. | |
| 6,306,302 | B1 | * | 10/2001 | Maree et al. | 210/605 |
| 6,387,669 | B1 | | 5/2002 | Truex et al. | |

FOREIGN PATENT DOCUMENTS

| DE | 33 21 515 | | 12/1984 |
|---|---|---|---|
| DE | 195 29 098 | | 2/1997 |
| EP | 0 411 687 | | 2/1991 |
| EP | 0 778 350 | | 6/1997 |
| EP | 0 819 756 | | 1/1998 |
| WO | 92/17410 | | 10/1992 |
| WO | 97/20778 | * | 6/1997 |
| WO | 97/29055 | | 8/1997 |
| WO | 99/06326 | * | 2/1999 |

OTHER PUBLICATIONS

"Hydrogen Sulfide Produced From Sulfate By Biological Reduction For Use In Metallurgical Operations", de Vegt et al., "Society For Mining, Metallurgy, And Exploration, Inc." Preprint 98–121, For Presentation at the SME Annual Meeting, Mar. 9–11, 1998.*

* cited by examiner

Primary Examiner—Stanley S. Silverman
Assistant Examiner—Ardith E Hertzog
(74) Attorney, Agent, or Firm—Young & Thompson

(57) ABSTRACT

A process is provided for the production of hydrogen sulphide from the bacterial reduction of a mixture of a liquid and elemental sulfur with an electron donor, such as hydrogen gas, carbon monoxide or organic compounds. The bacteria may be *Desulforomonas* sp. (mesophilic), *Desulfotomaculum* KT7 (thermophilic), etc. The liquid/sulfur mixture is at a pH ranging from 5 to 9, and the liquid/sulfur mixture contacts the bacteria at a hydraulic retention time of at least 1 day. The hydrogen sulphide is stripped from the liquid medium to produce a gas containing at least 1 volume percent hydrogen sulphide.

14 Claims, 2 Drawing Sheets

PROCESS FOR THE PRODUCTION OF HYDROGEN SULPHIDE FROM ELEMENTAL SULPHUR AND USE THEREOF IN HEAVY METAL RECOVERY

CROSS REFERENCE TO RELATED APPLICATION

This application is a continuation of prior U.S. application Ser. No.: 09/831,950, now abandoned, filed on 16 May 2001 as the 35 USC 371 national stage of International Application PCT/NL99/00705 filed on 16 Nov. 1999, which designated the United States of America.

TECHNICAL FIELD

The present invention is concerned with the production of hydrogen sulphide from elemental sulphur under mild conditions and with the use of the hydrogen sulphide in metal recovery.

BACKGROUND

Hydrogen sulphide is an expensive chemical used in the metallurgical and mining industry, but also in the electronic industry. It is used for example in nickel, zinc and copper mining and metallurgical operations for selective recovery and removal of metals from leach water streams, acid plant blow down streams, refinery electrolyte bleeds and precious metal plant bleeds. The required sulphide is normally:

(i) produced on site by catalytic reduction of elemental sulphur at elevated pressure and temperatures (above 150° C.) or transported to the site as liquefied hydrogen sulphide ($H_2S$) afterwards; such processes of chemical hydrogen sulphide production are known, e.g. from U.S. Pat. Nos. 4,094,961, 4,146,580 and 4,332,774;

(ii) transported to the site as a sodium sulphide solution (NaHS); or (iii) produced on site by the biological reduction of sulphate from diluted waste water streams (see e.g. WO 97/29055, U.S. Pat. No. 5,587,079).

These methods have disadvantages in that they are relatively expensive, require catalysts, introduce high salt, alkali or acid loads, and require more extensive safety precautions. WO 92/17410 discloses a process for removing sulphur compounds from water by anaerobic treatment with sulphur-reducing bacteria at high temperatures.

DESCRIPTION OF THE INVENTION

An improved process for the production of hydrogen sulphide has been found now. The process of the invention uses elemental sulphur, which is biologically reduced to hydrogen sulphide. The process has the following advantages compared to the above mentioned methods:

(a) Biological reduction of elemental sulphur can be carried out at mild temperature and pressure. Compared to catalytic reduction on site, the biological reduction is much safer and cheaper. Another advantage of the new process is that the production of sulphide is possible on a demand basis. The biological production of sulphide can be turned off and on very easily.

(b) Compared to adding a sodium sulphide (NaHS) in processes where sulphide is required, the biologically produced sulphide is less expensive and it has the advantage that no sodium enters the processes involved. Very often a low pH is required in the metallurgical operations, implying that more acid will have to be added when also sodium is added to the process. Furthermore the sodium will end up in a waste water stream as sodium sulphate which will has to be discharged or treated. Traditional lime treatment in this case however will not remove the sulphates as efficiently as before due to the presence of the sodium.

(c) Compared to the biological production of sulphide from a diluted sulphate containing waste water stream, the process of the invention has several advantages. It is much less expensive, due to the fact that only 25% of the amount of electron donor (hydrogen gas or organic compounds) is required for the reduction of elemental sulphur compared to the reduction of sulphate. Another advantage is that the pH in the bioreactor can be kept low, enabling a more efficient removal of the produced hydrogen sulphide from the liquid. Also, in the process of the invention water can be recycled to minimize the sulphide-containing liquid effluent to zero. In case of producing sulphide from sulphate present in a diluted waste water stream normally a post-treatment is required to oxidize the dissolved sulphide present in the effluent of the anaerobic reactor. Another advantage is that due to the fact that no liquid bleed is required; thus, bacteria can be retained in the reactor without a biomass retention system being necessary. This increases the active biomass concentration significantly and results in higher sulphide production rates.

The process of the invention can be carried out using a bioreactor which is fed with a concentrated elemental sulphur stream and an electron donor for the biological reduction of sulphur to produce hydrogen sulphide. As electron donor gaseous components like hydrogen and carbon monoxide can be used but also organic compounds such as ethanol, methanol, acetic acid or other fatty acids.

BIOLOGICAL CHARACTERISTICS

The bacteria: The biological reduction of sulphur is accomplished by a mixed culture of unidentified sulphur reducing bacteria such as species from the genera: *Desulforomonas* sp. (mesophilic), *Desulfotomaculum* KT7 (thermophilic), the species *Desulforolobus ambivalens, Acidianus infernus, Acidianus brierley, Stygiolobus azoricus* (mesophilic), *Thermoproteus neutrophilus, Thermoproteus tenax, Thermodiscus maritimus* (thermophilic), *Pyrobaculum islandicum, Pyrodictium occultum, Pyrodictium brockii* (hyperthermophilic), and other species of the genera *Desulfovibrio, Desulfotomaculum, Desulfomonas, Desulfobulbus, Desulfobacter, Desulfococcus, Desulfonema, Desulfosarcina, Desulfobacterium*, and *Desulforomas* (mesophilic), and species of sulphur-reducing methanogenic bacteria such as from the genera *Methanococcus* and *Methanobacterium*.

The electron donor: Hydrogen gas, carbon monoxide, alcohols (e.g. ethanol, methanol), fatty acids (e.g. acetic acid) or other readily degradable organic compounds.

The biological Conversions:

Hydrogen gas as electron donor: $H_2 + S^0 \rightarrow H_2S$

Organic compounds as electron donor e.g. ethanol:

$$C_2H_5OH + 6S^0 + 3H_2O \rightarrow 6H_2S + 2CO_2$$

Temperature: The process can be operated under mesophilic conditions (15–40° C.) or under thermophilic conditions (40–90° C.). The preferred temperature ranges are 25–75° C. Mesophilic temperatures for use with hydrogen are a particular aspect of the invention.

The pH: Operating between pH 5 and 9, preferably between 6 and 8.5, most preferably between 6 and 8.

Metals such as copper, zinc, nickel, cobalt, tin, lead, cadmium, bismuth, mercury, silver, iron, manganese, chromium, vanadium and titanium, can be recovered by contacting the hydrogen sulphide produced according to the invention with a liquid containing the metals and precipitating the metals as their sulphides. Such metals can also be recovered selectively using e.g. varying pH's as described in WO 97/29055.

After dewatering, the concentrated metal sulphide sludge can be processed using conventional metallurgical processes to recover the pure metal. For example, copper and zinc sulphides can be converted to elemental copper and zinc in roosting and melting processes combined with electrowinning. Especially favorable is the ECUPREX®-EW process for recovery of copper and lead, as this process produces elemental sulphur as a side product, and this side product can be used again for the production of the required hydrogen sulphide. This process is described in EP-A-411687. Copper and lead can thus be recovered from waste water or process streams by precipitation with hydrogen sulphide as insoluble copper sulphide or lead sulphide according to:

$$CuSO_4 + H_2S \rightarrow CuS + H_2SO_4 \qquad 1.$$

According to the ECUPREX®-EW process these metal sulphides are settled and dewatered and are then contacted with a fluoroboric leaching solution in which the metal dissolves and the sulphide is oxidized to elemental sulphur according to $$CuS + 2Fe(BF_4)_3 \rightarrow Cu(BF_4)_2 + 2Fe(BF_4)_2 + S^0 \qquad 2.$$

After separation of the elemental sulphur, electrolysis is used to produce pure copper at the cathode and to reoxidise the iron at the anode according to $$Cu(BF_4)_2 + 2e^- \rightarrow Cu + 2BF_4^-$$

$$2Fe(BF_4)_2 + 2BF_4^- \rightarrow 2Fe(BF_4)_3 + 2e^- \qquad 3.$$

After dewatering the sulphur slurry obtained in the leaching step (step 2) can be used for biological hydrogen sulphide production and the produced hydrogen sulphide is used again for the metal precipitation in step 1. In this way a perfect sulphur cycle has been created in which no sulphur compounds have to be purchased for the production of the hydrogen sulphide required to precipitate the metals in step 1.

DETAILED DESCRIPTION OF THE INVENTION

Process Design

Figure 1:
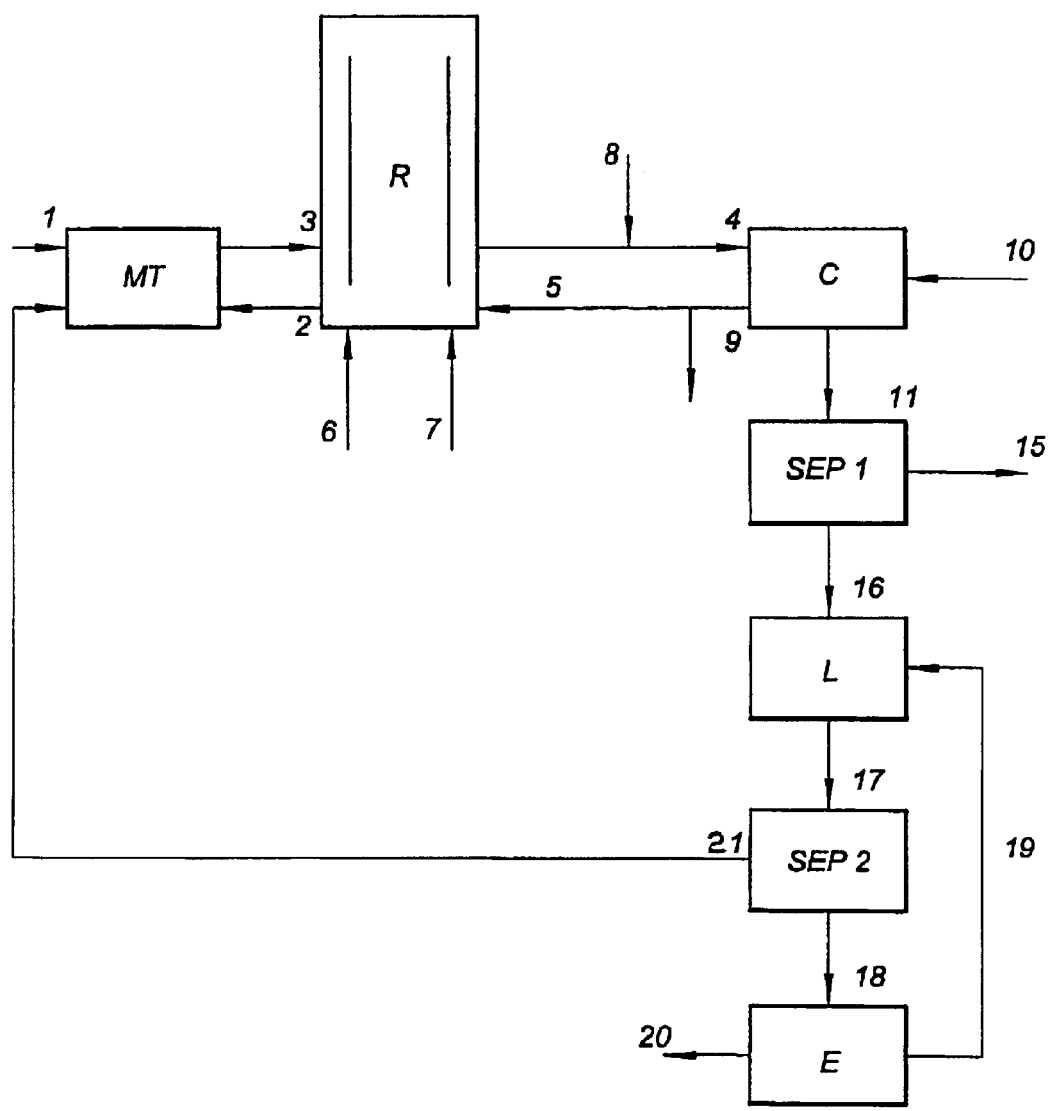
FIGS. 1 and 2 show alternative possible flow diagrams for the process of the invention.
Figure 2:
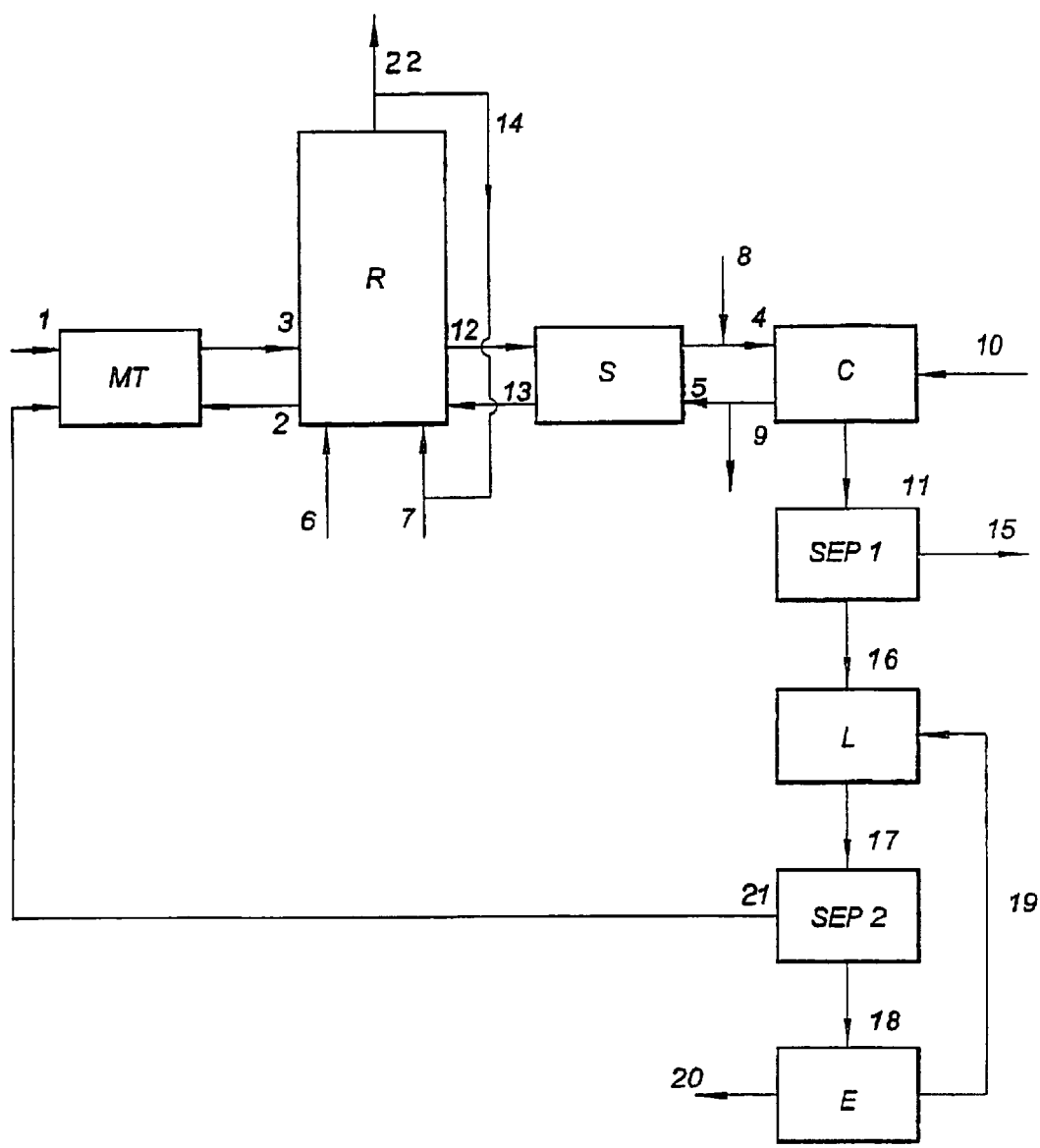

FIG. 1 shows a possible set-up for the process of the invention. Elemental sulphur (1) is preferably added in the form of ground particles which are either added directly to the reactor or preferably slurried up in the mixing tank (MT) using part of the reactor liquid (2) for this purpose prior to addition (3) to the bioreactor (R). In the anaerobic bioreactor an electron donor (organic compound (6) or hydrogen/carbon monoxide (7)) is added and the elemental Buiphur is reduced to produce hydrogen sulphide under ambient conditions. The bioreactor is well mixed in order to suspend the biomass and sulphur particles in the reactor and to create an effective contact between the two. Also the mixing prevents gradients of dissolved sulphide concentrations and pH through the reactor. Mixing can be achieved by different means, although it is preferred to mix the reactor using a gas recycle stream (4, and 5). Preferably a gas-lift loop type of reactor is used in this case to optimize the mixing characteristics of the reactor. A gas recycle is preferred for mixing because it provides an easy way to control the pH in the reactor and remove the produced hydrogen sulphide from the reactor by means of contacting the recycle gas with a process stream (10) in which the hydrogen sulphide is required. Another possible flow scheme would be to lead part of the liquid effluent (12) of the anaerobic bioreactor to a separate sulphide stripping column CS) with recycle (13) and remove the sulphide from this stream by contacting it either with a process gas stream (14) containing process gases (22) or a gas recycle stream (4, 5) over the contactor (C). This is shown in FIG. 2. A disadvantage of this flow scheme however is that the hydrogen sulphide is not removed from the liquid in the reactor itself. Applying a same pH in the bioreactor this will mean that the pH in the stripper will rise due to the removal of hydrogen sulphide resulting in a higher gas recycle flow required over the contactor unit to transport the same amount of hydrogen sulphide.

The contactor (C) is a device in which the hydrogen sulphide containing recycle gas is contacted with a process stream (10) to transfer the hydrogen sulphide from the recycle gas to the process stream. The design of the contactor and the process streams involved may be different for different applications. For example the contactor could be an open spray tower in which a metal containing process stream is contacted with the recycle gas. Metals will precipitate as metal sulphides and can be separated from the process stream downstream the contactor.

The process stream (10) may advantageously be a metal-containing stream (10) to which the hydrogen sulphide from the recycle gas is transferred. The metals will precipitate and the solid can be removed from the liquid downstream (11) the contactor in a solids separator (SEP 1). The design of the gas-liquid contactor is mainly dependent on gas flow rate, the liquid flow rate, the hydrogen sulphide concentration in the gas and the metal concentration in the liquid. An open spray tower or a packed column could e.g. be used for this purpose. After settling of the metal sulphides, the treated water (15) is discharged and the metal sulphides (16) are dewatered and can then be processed using conventional metallurgical processes to recover the pure metal. In case of the ECUPREX-EW process, the dewatered copper or lead sulphide sludge is contacted with the fluoroboric leaching solution (19) in the leaching reactor (L). In the second liquid-solids separator (SEP 2) the elemental sulphur (21) is separated from stream (17) and returned to the bioreactor (R). The dissolved metal containing solution (18) is led to the electrolysis unit (E) in which the pure metal is produced (20) and the fluoroboric leaching solution (19) is regenerated.

Instead of a metal-containing liquid, the process stream (10) fed to the contactor (C) may also be a liquid which absorbs the hydrogen sulphide in order to transport it to a regeneration column to concentrate the hydrogen sulphide to a higher percentage gas stream (>90%). The hydrogen sulphide gas stream can be used for the different industrial purposes of hydrogen sulphide. Furthermore, the contactor (C) may also be a membrane unit in which the hydrogen sulphide is selectively removed and concentrated to produce also a more highly concentrated gas stream to be used for different purposes in industry. It is also possible to strip the hydrogen sulphide directly from the bioreactor (R) or from stripper (S) using a process gas stream instead of using a gas recycle to transport the hydrogen sulphide to a liquid stream.

Process Control

In order to achieve high hydrogen sulphide production rates the process has to be controlled carefully. An important factor is the control of the pH in the water system (the water system comprises the reactor and optional stripper and connecting lines). The biological reduction of elemental sulphur using hydrogen gas, carbon monoxide or organic compounds as an electron donor results in the production of the acids hydrogen sulphide and carbon dioxide in the bioreactor. In principle this would lower the pH in the reactor to low levels which may inhibit the biological reactions. As no liquid bleed stream from the water system is desired, increasing the pH in the reactor by continuous addition of alkaline components such as sodium hydroxide is undesirable as the sodium concentration would build up to unacceptable levels inducing a liquid bleed stream at some level. The pH in the system is controlled by removing the acids from the liquid by stripping either directly from the reactor (FIG. 1) or from the effluent of the reactor (FIG. 2) in combination with the removal of the acid components from the recycle gas. The absence of a liquid bleed corresponds to a long hydraulic retention time of at least 1 day, preferably at least 5 days, up to 1 month or more, depending on the amount of water introduced with the elemental sulphur.

The process is a continuously operating system and all hydrogen sulphide produced is eventually removed from the liquid. However, the pH and the dissolved hydrogen sulphide concentration in the reactor can be selected freely. It can be maintained at a specific level by adjusting the electron donor feed to the removal of hydrogen sulphide in the contactor. The hydrogen sulphide concentration in the gas is kept high to be able to reduce the gas recycle flow for transporting the hydrogen sulphide and enhance mass transfer in the contactor. The hydrogen sulphide concentration in the gas is at least 1 vol. %, preferably at least 3 vol. %, more preferably at least 10 vol. %. As there is little or no liquid bleed from the bioreactor system, active biomass concentrations can be increased easily without installing a biomass retention system. This allows for higher tolerable dissolved hydrogen sulphide concentrations in the gas. Dissolved sulphide concentrations in the bioreactor are preferably at least 300 mg/l, especially at least 600 mg/l up to 3000 mg/l. Dissolved hydrogen sulphide concentrations above 3000 mg/l (above 20% in the gas) can be reached without loss of sulphide production capacity in the bioreactor. The biological production of hydrogen sulphide can be turned off instantaneously by interrupting the removal of hydrogen sulphide from the contactor. The hydrogen sulphide concentration will increase then and eventually inhibit the production of hydrogen sulphide. The process is reversible. Thus, after starting the removal of hydrogen sulphide again, the concentration in the bioreactor will decrease and hydrogen sulphide production will resume immediately. Another way of stopping and starting the production instantaneously is by stopping and continuing the electron donor supply.

Hydrogen sulphide is removed as an acid in the contactor (C) and the produced carbon dioxide is removed by purging part of the gas (9) from the gas recycle system. The amount of carbon dioxide purged can be controlled by controlling the amount of an inert gas e.g. nitrogen gas (8) added to the recycle gas for this reason. The surplus gas resulting from the carbon dioxide purge is separated from the hydrogen sulphide and then removed.

EXAMPLE 1

In a 5 litre gas lift loop reactor 1.25 g/h of ground elemental sulphur was added by means of pumping from a tank in which the ground sulphur was mixed with liquid from the bioreactor. Hydrogen gas was added as electron donor for the biological reduction. No make-up water was used and no liquid bleed existed. The reactor was operated at 35° C. and the pH in de reactor was maintained at 7.5 by stripping the hydrogen sulphide from the liquid with the recycle gas. The recycle gas was contacted with leach water (7 litre/h) containing copper removing the acid hydrogen sulphide from the recycle gas and recovering the copper as copper sulphide from the leach water. Dissolved hydrogen sulphide concentrations up to 2000 mg/l were found. The hydrogen sulphide concentration in the gas reached up to 15%.

EXAMPLE 2

In a 8 litre laboratory reactor 80 grams of ground elemental sulphur was added daily and ethanol was continuously added as electron donor for the reduction. The reactor was operated at 30° C. and the pH was controlled at pH 7 applying a gas recycle to strip out the hydrogen sulphide and carbon dioxide. The hydrogen sulphide was removed from the recycle gas by contacting the gas with a copper sulphate containing solution in a bubble column. Carbon dioxide was removed by adding small amount of nitrogen gas to the recycle gas creating a gas purge stream containing nitrogen, carbon dioxide and small amounts of hydrogen sulphide. Dissolved hydrogen sulphide concentrations up to 1500 mg/l were found. The hydrogen sulphide concentration in the gas reached up to 20%.

What is claimed:

1. A process for the production of hydrogen sulphide by reduction of a sulphur source, which comprises:
   providing elemental sulphur;
   providing a liquid;
   mixing the elemental sulphur with the liquid to obtain a liquid medium;
   subjecting the liquid medium at a pH between 5 and 9 to an anaerobic biological treatment in a bioreactor in the presence of sulphur-reducing bacteria as a catalyst, and hydrogen gas, carbon monoxide or organic compounds as an electron donor, and at a hydraulic retention time of at least 5 days; and
   stripping the resultant hydrogen sulphide from the liquid medium to produce a gas containing at least 1 vol. % of hydrogen sulphide.

2. The process according to claim 1, wherein a sulphide concentration of at least 300 mg/l is maintained in the bioreactor.

3. The process according to claim 2, wherein the sulphide concentration is at least 600 mg/l.

4. The process according to claim 3, wherein the sulphide concentration is at least 3000 mg/l.

5. The process according to claim 1, further comprising a step of subsequently contacting the sulphide gas with a heavy metal containing stream to precipitate metal sulphides.

6. The process according to claim 5, wherein the metal sulphides are subsequently treated to produce elemental sulphur, which is recycled to the bioreactor.

7. The process according to claim 5, wherein the heavy metal comprises at least one of copper and lead.

8. The process according to claim 1, wherein a sulphide gas containing at least 3 vol. % of hydrogen sulphide is produced.

9. The process according to claim 8, wherein a sulphide gas containing at least 10 vol. % of hydrogen sulphide is produced.

10. The process according to claim 1, wherein hydrogen gas is used as the electron donor.

11. The process according to claim 10, wherein a temperature of 15–40° C. is maintained in the bioreactor.

12. The process according to claim 1, wherein the hydrogen sulphide is stripped from the bioreactor, at such a rate that a pH between 6 and 8.5 is maintained in the bioreactor.

13. The process according to claim 1, wherein carbon dioxide is stripped from the liquid medium by addition of an inert gas; said carbon dioxide being subsequently separated from hydrogen sulphide.

14. The process according to claim 1, further comprising a step of concentrating the hydrogen sulphide in the produced gas.

* * * * *